US011744839B2

(12) United States Patent
Ryu et al.

(10) Patent No.: US 11,744,839 B2
(45) Date of Patent: Sep. 5, 2023

(54) METHOD OF INCREASING PLATELET COUNTS OF A SUBJECT

(71) Applicants: KOREA BASIC SCIENCE INSTITUTE, Daejeon (KR); University of Louisville Research Foundation, Inc., Louisville, KY (US); Max-Planck-Gesellschaft zur Foerderung der Wissenschaften e.V., Munich (DE)

(72) Inventors: Kyoung-Seok Ryu, Daegu (KR); Myeongkyu Kim, Gottingen (DE); Christian Griesinger, Louisville, KY (US); Donghan Lee, Louisville, KY (US)

(73) Assignees: KOREA BASIC SCIENCE INSTITUTE, Daejeon (KR); University of Louisville Research Foundation, Inc., Louisville, KY (US); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 17/224,368

(22) Filed: Apr. 7, 2021

(65) Prior Publication Data

US 2022/0339170 A1    Oct. 27, 2022

(51) Int. Cl.

| | | |
|---|---|---|
| A61K 31/00 | (2006.01) |
| A61K 31/655 | (2006.01) |
| A61K 38/12 | (2006.01) |
| A61K 31/4245 | (2006.01) |
| A61K 31/426 | (2006.01) |
| A61K 31/4196 | (2006.01) |
| A61K 31/506 | (2006.01) |
| A61K 31/404 | (2006.01) |
| A61K 31/343 | (2006.01) |
| A61K 31/4184 | (2006.01) |
| A61K 31/55 | (2006.01) |
| A61K 31/4709 | (2006.01) |
| A61K 31/4422 | (2006.01) |
| A61K 31/4725 | (2006.01) |
| A61K 31/196 | (2006.01) |
| A61K 31/4402 | (2006.01) |
| A61K 31/4418 | (2006.01) |
| A61K 31/41 | (2006.01) |

(52) U.S. Cl.
CPC .......... *A61K 31/655* (2013.01); *A61K 31/196* (2013.01); *A61K 31/343* (2013.01); *A61K 31/404* (2013.01); *A61K 31/41* (2013.01); *A61K 31/4184* (2013.01); *A61K 31/4196* (2013.01); *A61K 31/426* (2013.01); *A61K 31/4245* (2013.01); *A61K 31/4402* (2013.01); *A61K 31/4418* (2013.01); *A61K 31/4422* (2013.01); *A61K 31/4709* (2013.01); *A61K 31/4725* (2013.01); *A61K 31/506* (2013.01); *A61K 31/55* (2013.01); *A61K 38/12* (2013.01)

(58) Field of Classification Search
CPC .. A61K 31/655; A61K 31/196; A61K 31/343; A61K 31/404; A61K 31/41; A61K 31/55; A61K 38/12
See application file for complete search history.

(56) References Cited

U.S. PATENT DOCUMENTS 10,543,286 B2    1/2020    Bahou et al.

OTHER PUBLICATIONS

Van Dijk, R., Aronson, S.J., de Waart, D.R. et al. Biliverdin Reductase inhibitors did not improve severe unconjugated hyperbilirubinemia in vivo . Sci Rep 7, 1646 (2017).*
Paukovich, N., et al.; "Biliverdin Reductase B Dynamics Are Coupled to Coenzyme Binding", J Mol Biol (2018) 430, 3234-3250.
Rittirsch, D., et al.; "Improvement of prognostic performance in severely injured patients by integrated clinico-transcriptomics: a translational approach", Critical Care (2015) 19:414.

\* cited by examiner

*Primary Examiner* — Jeanette M Lieb
(74) *Attorney, Agent, or Firm* — Harness, Dickey & Pierce, P.L.C.

(57) ABSTRACT

Method of increasing platelet counts in a subject, the method comprising administering to the subject a therapeutically effective amount of a compound that inhibits Biliverdin reductase B (BLVRB) activity by blocking a binding site of BLVRB or a pharmaceutically acceptable salt thereof, wherein the compound does not contain xanthene or acridine moiety is provided.

6 Claims, 6 Drawing Sheets

A

Phloxine B

Erythrosin B

METHOD OF INCREASING PLATELET COUNTS OF A SUBJECT

FIELD

The present disclosure relates generally to a method of increasing platelet counts in a subject.

BACKGROUND

Platelets, or thrombocytes, are small, colorless cell fragments in our blood that form clots and stop or prevent bleeding. The regulation of platelet population and the control of specific platelet responses are prominent targets for new drugs against platelet disorders. The impairment of platelet regulation leads to various bleeding disorders including thrombocytopenia that is characterized by increased bleeding (hemophilia) due to low platelet counts. A typical treatment intervention for thrombocytopenia is the increase in platelet counts by the induction of platelet generation or platelet transfusion. On the other hand, thrombocytosis is characterized by excessive platelets in the blood as opposed to the symptom of thrombocytopenia. Through cohort analysis of thrombocytosis with large-scale platelet transcriptome sequencing in both primary (essential) and secondary (reactive) thrombocytosis cohorts, it was found that Biliverdin reductase B (BLVRB) has an ability to control the production of platelet through MK differentiation by reactive oxygen species (ROS) control. Furthermore, it has been shown that the loss-of-function mutant (BLVRB$^{S111L}$) induces more platelets by ROS accumulation, and thus, the inhibition of BLVRB activity represents a novel strategy to increase the platelet generation due to a unique BLVRB specific redox-regulation in the heme degradation pathway.

To achieve the inhibition of BLVRB activity, xanthene dyes and acridine-containing compounds, of which structures are similar to that of flavin mononucleotide (FMN), a natural BLVRB substrate, have been derived. Among these xanthene dyes, erythrosin B and phloxine B were found to be the two most potent inhibitors. However, chronic administration of erythrosin B was shown to promote thyroid tumors in rats. Furthermore, through careful investigation with NMR and dynamic light scattering (DLS) experiments, we verified that erythrosin B and phloxine B induce multimerization of BLVRB, which can cause potential complications to use erythrosin B and phloxine B as therapeutics. Thus, new drug candidates inhibiting BLVRB are in need for platelet disorders.

SUMMARY

The present disclosure provides a method of increasing platelet counts in a subject, comprising administering to the subject a therapeutically effective amount of a compound that inhibits Biliverdin reductase B (BLVRB) activity by blocking a binding site of BLVRB or a pharmaceutically acceptable salt thereof, wherein the compound does not contain xanthene or acridine moiety.

In one embodiment of the disclosure, the compound shows IC$_{50}$ of less than 5 μM.

In one embodiment of the disclosure, the compound is selected from the group consisting of the following formulae 1 to 20.

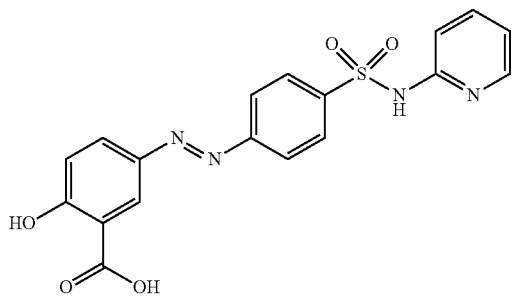

[Formula 1]

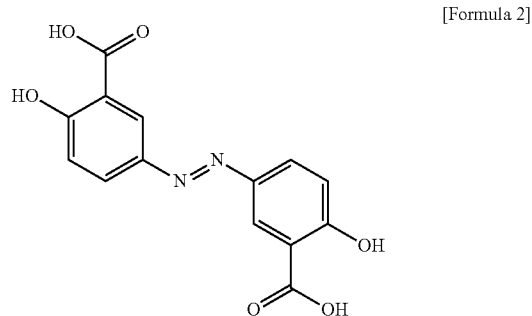

[Formula 2]

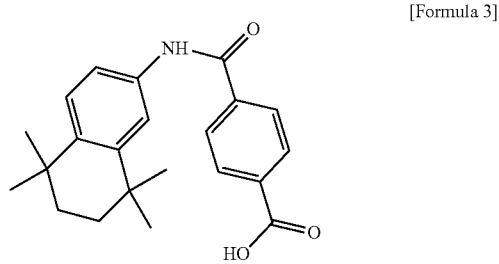

[Formula 3]

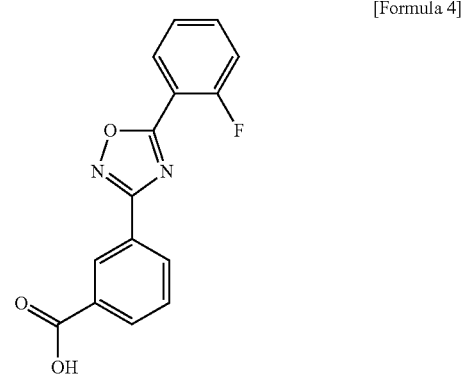

[Formula 4]

[Formula 5]
[Formula 6]
[Formula 7]
[Formula 8]
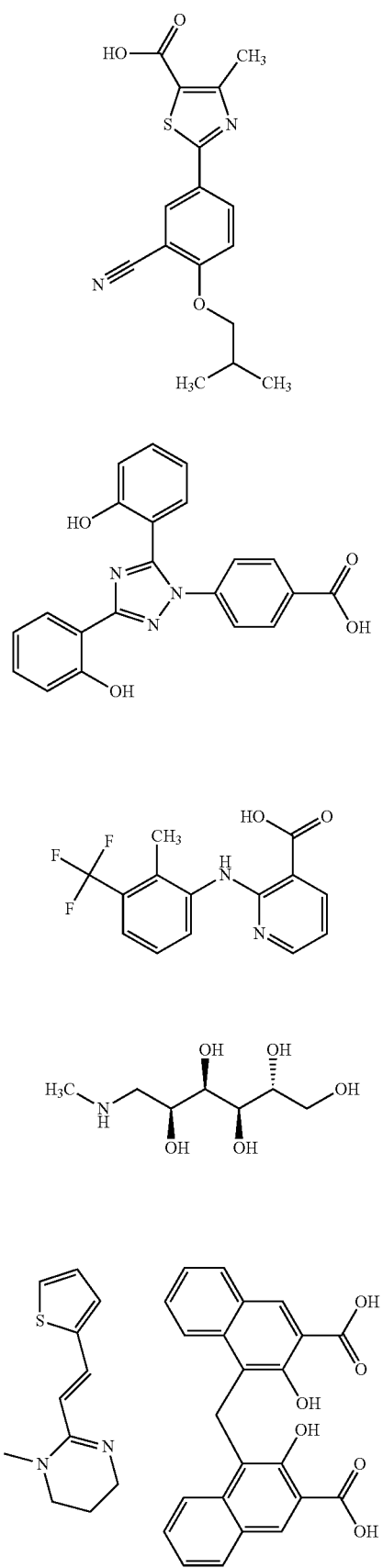
[Formula 9]
[Formula 10]
[Formula 11]
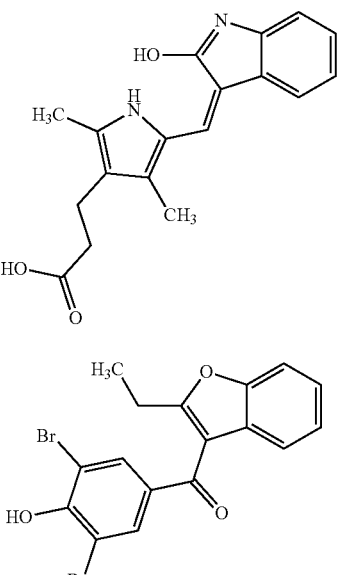
[Formula 12]
[Formula 13]
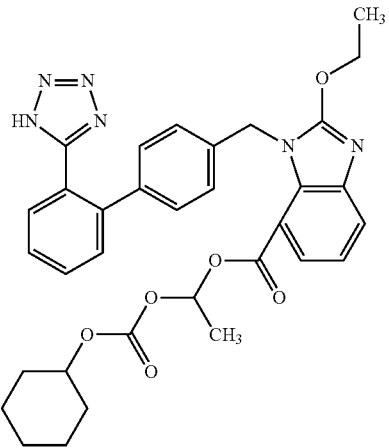

[Formula 14]

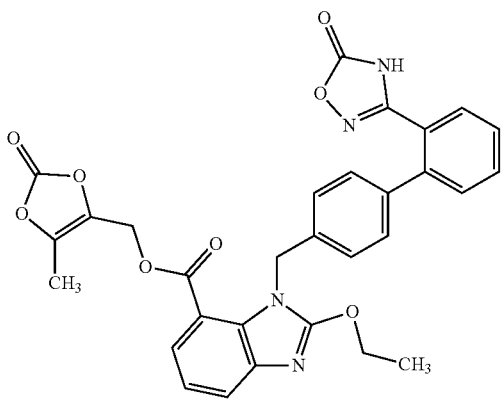

[Formula 15]

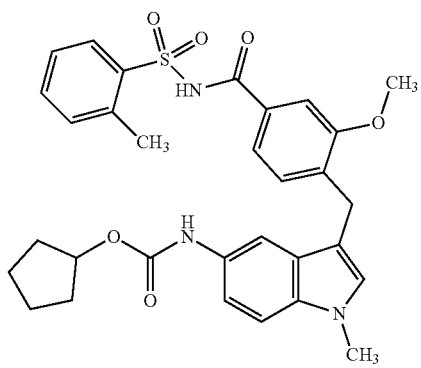

[Formula 16]

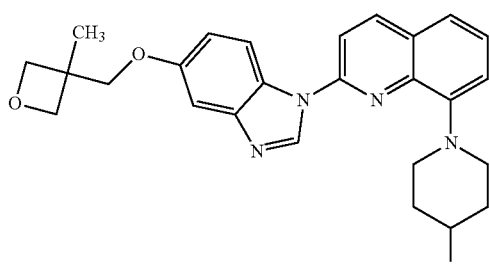

[Formula 17]

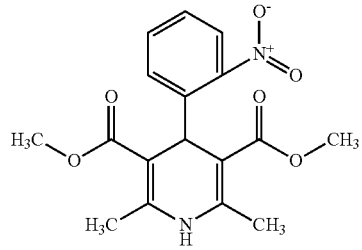

[Formula 18]

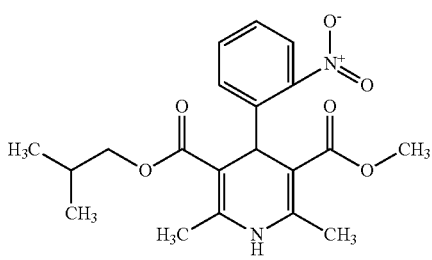

[Formula 19]

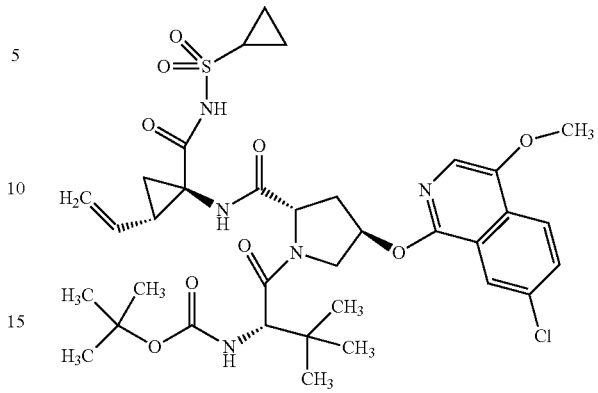

[Formula 20]

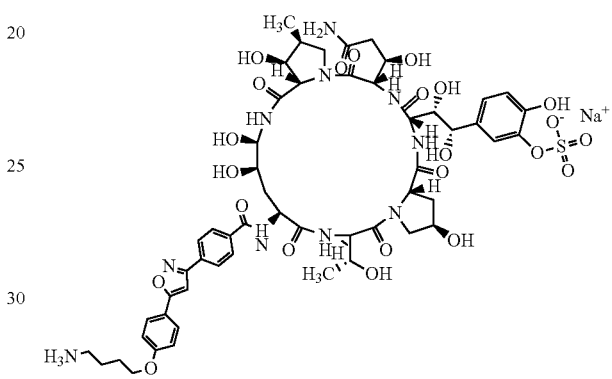

In one embodiment of the disclosure, the compound is administered in the form of a composition further comprising a pharmaceutically acceptable vehicle.

In one embodiment of the disclosure, the increase of platelet counts treats platelet disorder.

In one embodiment of the disclosure, the platelet disorder is thrombocytopenia.

Further, the present disclosure provides a method of treating platelet disorder, comprising administering to a subject in need a therapeutically effective amount of a compound selected from the group consisting of formulae 1 to 20 above or a pharmaceutically acceptable salt thereof.

DETAILED DESCRIPTION

Figure 1A:
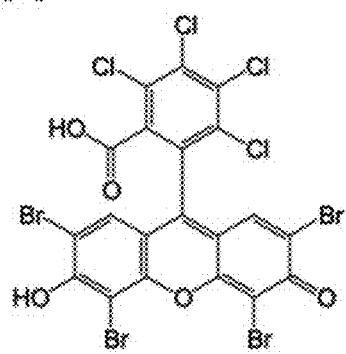
FIG. 1A shows molecular structures of xanthene-based drug candidates, Phloxine B and Erythrosin B.
Figure 1A:
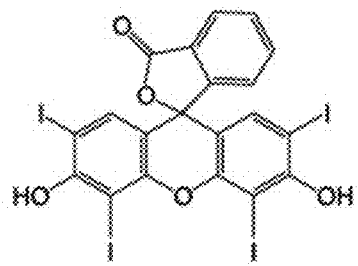

While the present invention is open to various modifications and alternative embodiments, specific exemplary embodiments thereof will be described and illustrated by way of example in the accompanying drawings. However, it is to be understood that the present invention is not limited to a specific disclosed form but includes all modifications, equivalents, and substitutions without departing from the scope and spirit of the present invention.

It will be further understood that the terms "comprise," "comprising," "include," and/or "including," when used herein, specify the presence of stated features, numbers, steps, operations, elements, components, or combinations thereof but do not preclude the presence or addition of one or more other features, numbers, steps, operations, elements, components, and/or combinations thereof.

As used herein, the term "therapeutically effective amount" refers to an amount of a compound sufficient to show a desired biological response, or the development or relief of symptom or indications.

As used herein, the term "subject" refers to an individual to which the compound is to be administered by the method of the present disclosure, and may include not only humans but also animals.

As used herein, the term "treatment" means that a desired therapeutic effect is implemented in the subject, and includes a reduction in progression rate, cessation of progression, relief of symptoms, improvement of a condition, and healing of a condition. In addition, the term "prevention" may mean use for a subject who has not yet developed a disease but who is at risk of developing a disease.

Platelets are cell fragments that circulate in the bloodstream and help blood clot. The platelet count (the platelet count circulating in the bloodstream) is usually about 140,000 to 440,000 per microliter ($140 \times 10^9$ to $440 \times 10^9$ per liter). "Platelet disorder" refers to an abnormal increase or decrease in the count of such platelets, or impaired platelet function, and includes "thrombocytopenia."

"Thrombocytopenia" is a disease that causes abnormal bleeding symptoms as the count of platelets decreases.

Thrombocytopenia may occur even when platelet production in the bone marrow decreases or platelet destruction in the spleen increases. Platelet production in the bone marrow is affected by leukemia, aplastic anemia, or anti-cancer therapy. In addition, thrombocytopenia is not known for its exact cause, but may occur in the case of developing a regulatory mechanism or metabolic disorder; in the case of exposure to drugs or chemicals; or in the presence of a blood disease such as megaloblastic anemia, leukemia or histocytosis, an infectious disease such as hepatitis, and acquired immunodeficiency syndrome, or an autoimmune disease such as systemic lupus erythematosus. In rare cases, thrombocytopenia may occur due to a malignant tumor.

The most important function of platelets is hemostasis, and so bleeding symptoms develop when thrombocytopenia occurs. If the platelet count is less than 20,000 per 1 $mm^3$, bleeding can occur naturally without damage to the blood vessels, and severe gastrointestinal tract or central nervous system bleeding occurs. Bleeding also occurs on the skin or mucous membranes, which appear as purpura, hematuria, and nasal bleeding, etc. Prolonged bleeding leads to anemia. Thus, thrombocytopenia may cause or worsen anemia or may cause complications of anemia.

Biliverdin reductase B (BLVRB) is an enzyme protein known to control platelet count through the control of reactive oxygen species (ROS). It is expected that the platelet count can be increased by controlling the activity of BLVRB. Accordingly, research is being conducted as a target for the treatment of platelet disorders including thrombocytopenia. Conventionally, xanthene or acridine-based compounds have been used as inhibitors of BLVRB activity, but there is a concern of complications due to cytotoxicity and oligomerization of BLVRB. However, according to an aspect of the present disclosure, platelet count can be increased by administering to a subject a compound capable of inhibiting BLVRB by blocking the binding site of BLVRB and containing no xanthene or acridine moiety.

The compound may include the compounds of formulae 1 to 20 described above, which have an $IC_{50}$ value of less than 5 µM. In addition, the compound of the present disclosure may have a reaction enthalpy (ΔH) of less than −7 kcal/mol. Among these compounds, the compounds of formulae 1 to 8 are water-soluble.

The compound according to the present disclosure may be used in the form of a pharmaceutically acceptable salt. The "pharmaceutically acceptable salt" refers to a salt of a compound that maintains the pharmacological activity of the parent compound, and includes, but is not limited to, for example, (i) a salt formed with an inorganic acid such as hydrochloric acid, hydrobromic acid, sulfuric acid, nitric acid, and phosphoric acid; (ii) a salt formed with organic acids such as acetic acid, propionic acid, isobutyric acid, glycolic acid, lactic acid, pyruvic acid, malonic acid, succinic acid, glutaric acid, fumaric acid, malic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid; (iii) a salt formed when acidic protons present in the parent compound are replaced by metal ions, for example, alkali metal ions, alkaline earth metal ions, or aluminum ions; or (iv) a coordination with an organic base such as ethanolamine, diethanolamine, triethanolamine, or N-methylglucamine.

In addition, in the method according to the present invention, the compound or a pharmaceutically acceptable salt thereof may be used alone, but in addition to this, a composition further comprising a pharmaceutically acceptable carrier, specifically in the form of a pharmaceutical composition may be used. The pharmaceutically acceptable carrier may be one commonly used in the pharmaceutical field, and an excipient (e.g., starch, calcium carbonate, sucrose, lactose, sorbitol, mannitol, cellulose, etc.) or a diluent (e.g., physiological saline, purified water, etc.).

In addition, if necessary, the composition of the present disclosure may further comprise pharmaceutically acceptable additives other than the pharmaceutically acceptable carrier, for example, a binder, a disintegrant, a lubricant, a coating agent, a film coating base, an enteric film coating base, a soft capsule base, a solubilizing aid, an emulsifying agent, a suspending agent, a stabilizer, a buffering agent, an antioxidant, a surfactant, a sweetening agent, a flavoring agent, a preservative, a thickening agent, a fragrance, or a coloring agent.

The compound of the present disclosure may be administered orally or parenterally. The parenteral administration may be intravenous injection, subcutaneous injection, intramuscular injection, intraperitoneal injection, endothelial administration, topical administration, intranasal administration, intrapulmonary administration, and rectal administration, etc. When administered orally, the compound of the present disclosure may be formulated in the form of a solid or liquid formulation. The solid formulation may be, for example, tablets, capsules (soft & hard capsules), powders, granules, pills, troches, etc., and the liquid formulation may be, for example, elixirs, suspensions, emulsions, solutions, syrups, lemonades, etc. In the case of tablets, in addition to the active ingredient, carriers such as lactose and corn starch, etc., lubricants such as magnesium stearate, etc., binders such as methylcellulose, microcrystalline cellulose, etc., polyvinyl alcohol, and disintegrants such as bentonite, sodium alginate, etc. may be usually added. In the case of a liquid formulation, the active ingredient may be formulated with a carrier such as purified water or physiological saline, and a dissolution aid such as sucrose monostearate, or a stabilizer such as polyvinylpyrrolidone, etc., if necessary. In the case of oral aqueous suspension, the active ingredient may be formulated with a suspending agent and, if necessary, a surfactant, a preservative, a stabilizer, etc.

The dosage of the compound may be determined in consideration of the method of administration, the age and sex of the subject, the severity, the condition, the inactivation rate, and the drug to be used in combination, and may be administered once or more a day.

The present disclosure is further described by the following non-limiting examples:

EXAMPLES

Materials and Chemicals

All salts, physiological buffers, FMN, NADPH, NADP$^+$, phloxine B, erythrosin B and 10×PBS were purchased from Sigma Aldrich (St. Louis, Mo., USA), unless otherwise specified. $^{13}$C/$^{15}$N isotopes, DMSO-d6 were purchased from Cambridge Isotope Laboratories. All compounds of formulae 1 to 20 were obtained from APExBIO (Houston, Tex., USA). The compounds of formulae 1 to 20 were dissolved in DMSO or DMSO-d6, and stock solutions were stored at −80° C.

Example 1: Multimerization of BLVRB

Figure 1B:
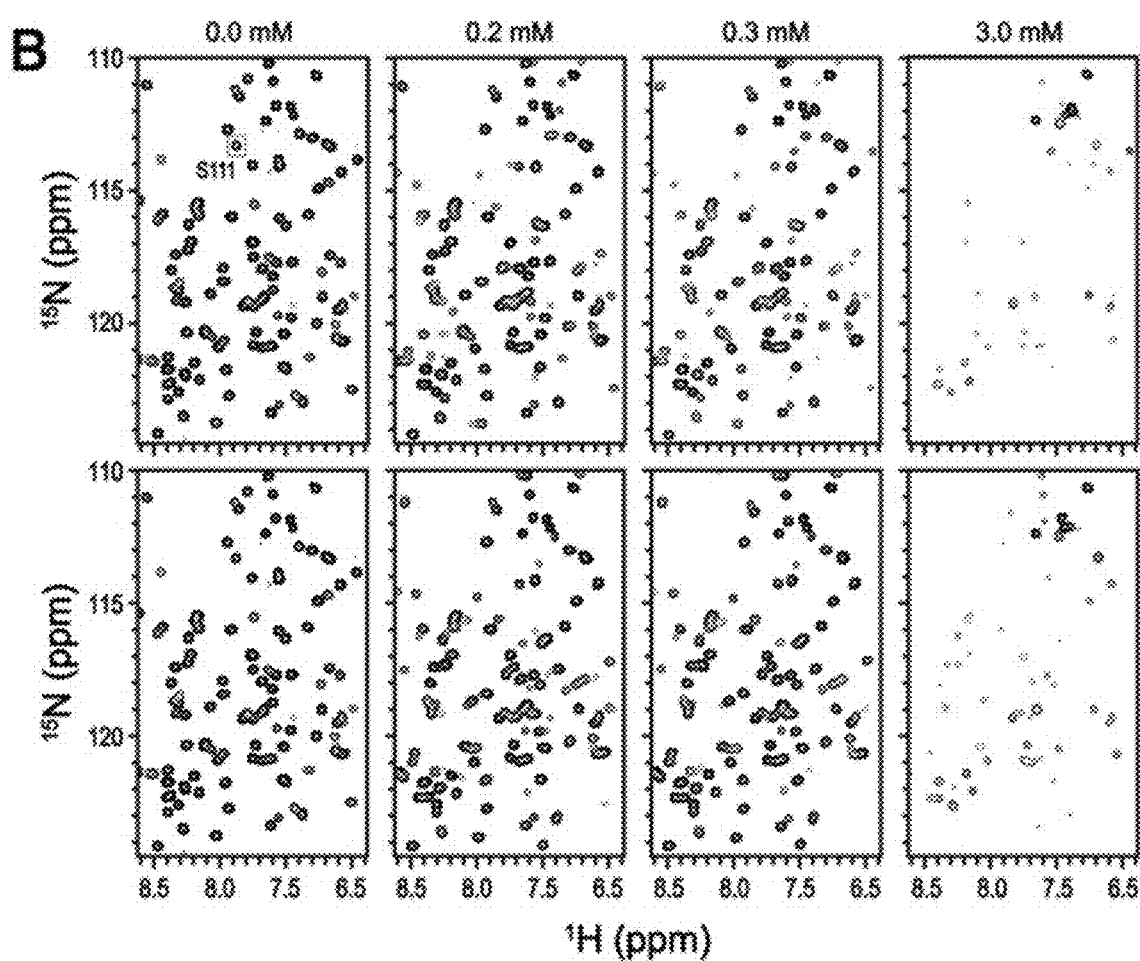
FIG. 1B shows a result from NMR titration experiment with phloxine B (top) and erythrosin B (bottom). Ratio 1:0, 1:0.6, 1:1, 1:10 [Half-holo form of BLVRB (0.3 mM): phloxine B and erythrosin B].
Figure 2A:
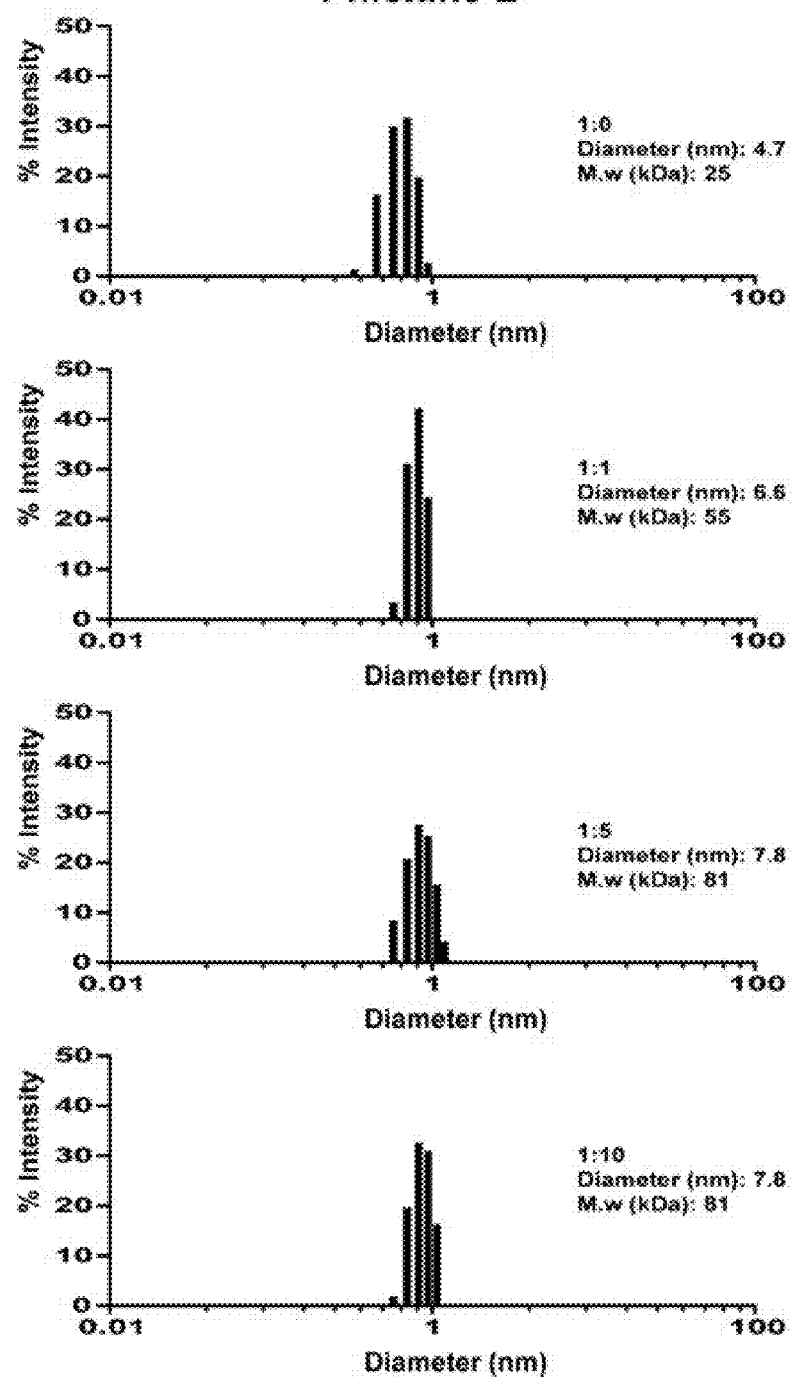
FIGS. 2A and 2B show DLS results of BLVRB depending on the concentration of phloxine B (FIG. 2A) and erythorosin B (FIG. 2B). Molar ratio of the sample is 0, 1, 5, 10 [erythrosin B or phloxine B/BLVRB]. The horizontal axis represents the diameter of each drug on a logarithmic scale. The vertical axis represents the relative intensity of the signal.
Figure 2B:
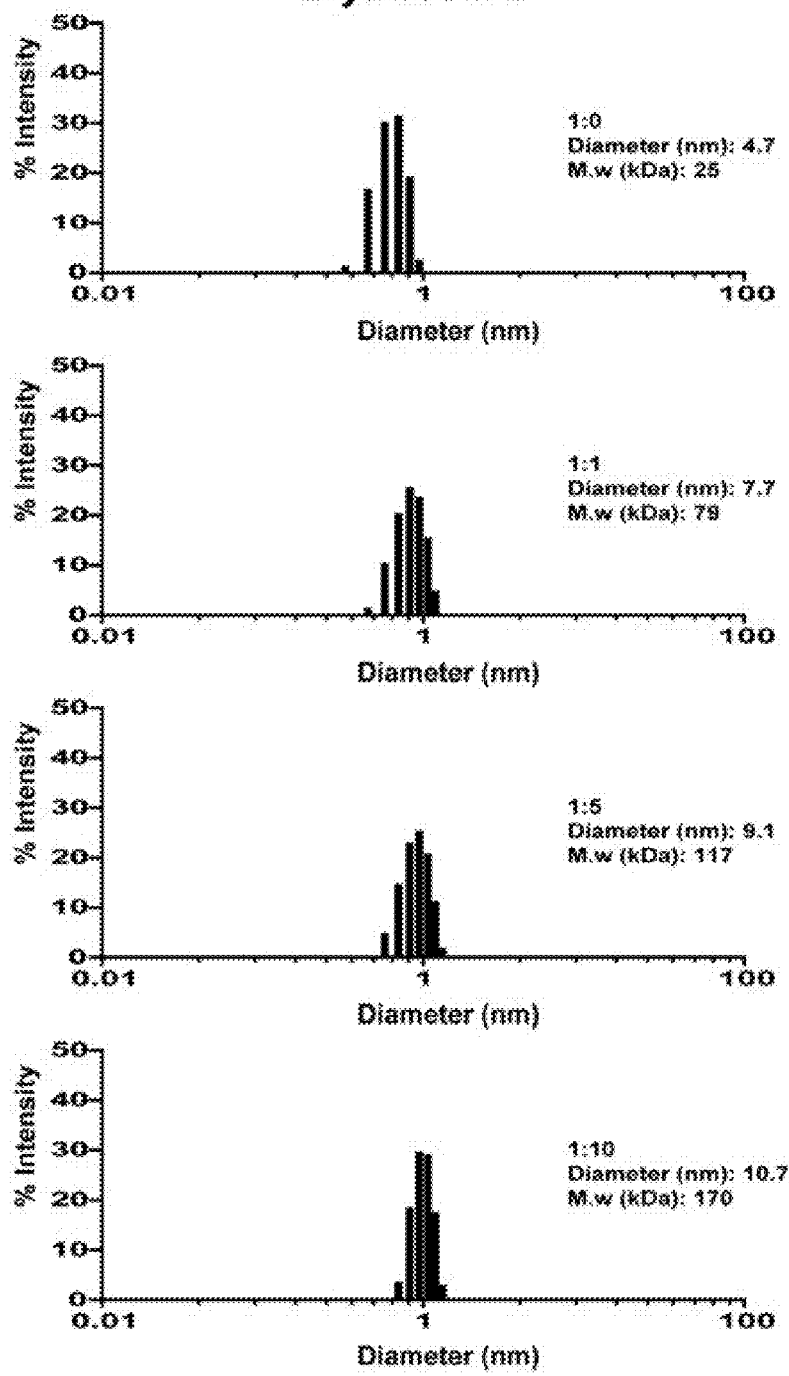

Erythrosin B and phloxine B are recognized as the two most potent inhibitors for BLVRB. The inhibition mechanism of these two compounds was investigated in physiological environment by NMR. As shown in FIG. 1B, when the concentration of erythrosin B or phloxine B was increased, it was observed that backbone amide signals disappeared and only certain side chain peaks remained visible. This indicates multimerization of BLVRB upon the addition of erythrosin B and phloxine B. The result is also corroborated with DLS of FIG. 2 showing an increase in the size of the BLVRB-inhibitor complex upon the concentration increase of erythrosin B or phloxine B. Thus, the inhibition mechanism of erythrosin B and phloxine B may not only be due to blocking of the active site in BLVRB but also due to multimerization of BLVRB, which may cause complications to control spatial control in subcellular scale.

Example 2: Enzyme Activity Assay

Figure 3:
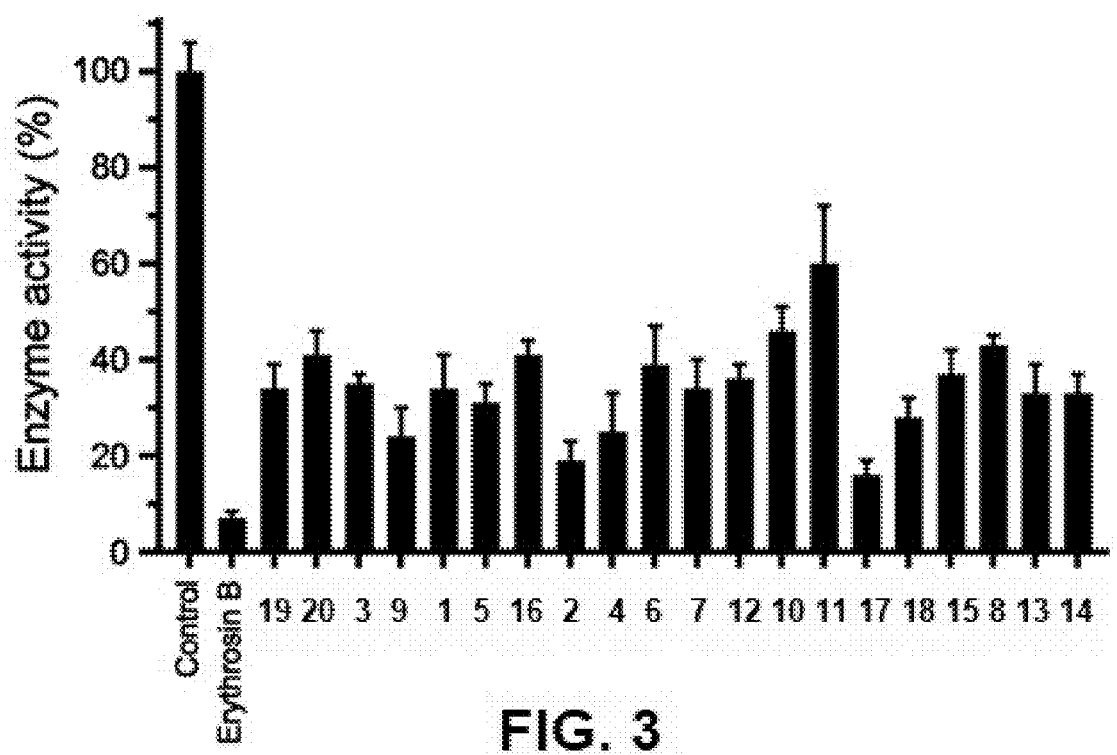
FIG. 3 is graphs showing Enzyme activities (%) of the compounds of the present disclosure. Control was measured in the absence of any compounds and all experiments repeated 3 times.

An enzyme activity assay for BLVRB was conducted. Since BLVRB catalyzes the NAD(P)H dependent readuction of FMN, changes in the NAD(P)H concentration in the presence of FMN can be used to measure enzyme activity in the absence (control) and presence of drug candidates. The $IC_{50}$ (the concentration of the drug candidate at which BLVRB activity to convert NADPH to NADP$^+$ in the presence of FMN was reduced to 50%) was used as the selection criterion for the screenings of more potent inhibitory molecules with lower $IC_{50}$ value. Native form of BLVRB (without NADP$^+$) was used for enzyme activity assay. Assay was performed by monitoring the rate of oxidation of NADPH at 340 nm with Gemini EM Microplate Reader. All assays were operated at 25° C. in 100 mM Phosphate-buffered saline, 0.01% of triton X-100, 100 µM FMN, 100 µM NADPH, 1 µM BLVRB and variable concentration of compounds of the present disclosure. The control reactions were carried out in the absence of compounds of the present disclosure to compare the effectiveness of the drug. FMN and NADPH were freshly constructed with 10 mM stock daily, calculated by UV/Vis spectrometer. In each case, FMN was added to initiate the reaction and measured for 30 minutes. The concentration of the compounds of the present disclosure was sequentially decreased in the order of 100 µM, 25 µM, and 5 µM. Through this procedure, 20 inhibitors whose $IC_{50}$ was less than 5 µM were found as shown in FIG. 3.

Example 3: NMR Titration Experiments

Protein-based NMR spectroscopy is one of the most well-suited methods to identify intermolecular interactions including small molecule and protein interactions. Further, protein-based NMR methods provide information on binding sites, which is of prime interest for optimizing small molecules. Therefore, HSQC experiments of $^{15}$N-labeled BLVRB were performed by titrating increasing amounts of the subject compounds to monitor the chemical shift changes upon the binding of the compounds identified in the enzyme activity assay. In particular, Ser111 was previously identified as a key residue involved in the catalytic mechanism of BLVRB. Thus, we monitored chemical shift changes of the Ser111 amide signal in HSQC spectra and found that 8 FDA-approved drugs binding to BLVRB shift the amide resonances of Ser111. Using the assignment, the chemical shift perturbations (CSPs) of BLVRB by each drug were extracted from the spectra and the binding site of each drug was identified based on the CSPs.

Half-holo form of BLVRB (with NADP$^+$) was used for NMR experiments. All the subject compounds were dissolved in DMSO-d$_6$. NMR titration and 1D experiments were operated at a $^1$H frequency of 800 MHz using a Bruker Avance spectrometer. All experiments were performed at 298 K and 5 mm diameter NMR tubes with a sample volume 500 µL were used.

Figure 4:
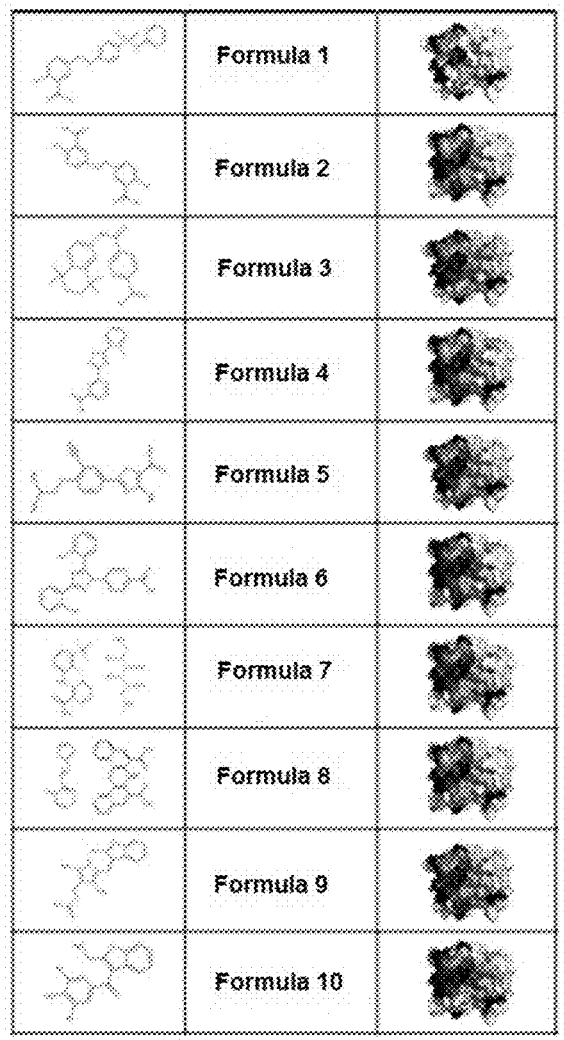
FIG. 4 shows the surface representation of BLVRB colored according to the chemical shift perturbation values of the main-chain amides.
Figure 4:
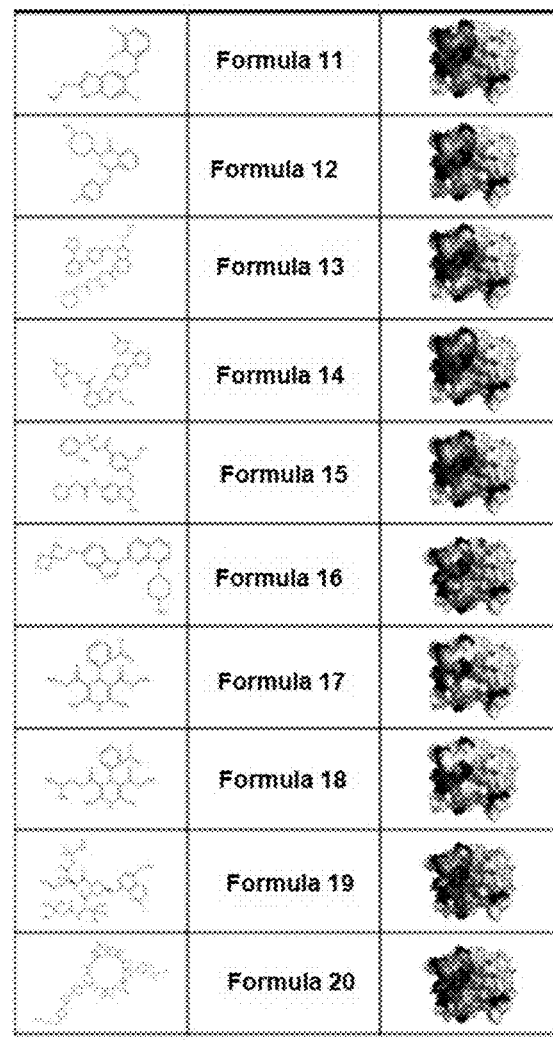

It was concluded that all compounds of the present disclosure bind to the substrate binding pocket of BLVRB and especially, Ser 111, which is the most critical residue for the enzyme activity thereby inhibiting the binding of a substrate such as FMN or biliverdin IXβ. Verification of drug binding effect on the BLVRB surface was also successfully performed by analyzing CSPs and mapping on the surface structure of the BLVRB. FIG. 4 shows the surface representation of BLVRB colored according to the chemical shift perturbation values of the main-chain amides.

Example 4: Isothermal Titration Calorimetry

ITC is a method to directly measure heat produced during complex formation at constant temperature. The thermodynamic quantities characterizing the complex: ΔH and ΔS can be characterized. Those values for the compounds of formulae 1 to 8 as well as xanthene-based compounds (erythrosin B and phloxine B) to BLVRB were determined. All ITC experiments were measured at 25° C., i.e. the same temperature at which enzyme activity and NMR experiments were performed. ITC experiment was performed using Microcal Auto-iTC200 (Malvern Instruments, UK) at 25° C. The calorimetric cell (200 μL) contained 0.07 mM BLVRB, dissolved in buffer (pH 6.5, 50 mM Bis-Tris, 50 mM NaCl, 0.1 mM TCEP). The compounds of the present disclosure (0.65~1.1 mM) in the syringe (40 μL) were titrated into BLVRB (0.07 mM). Each experiment comprised that ligands were injected 19 times with 2 μL aliquots into the 200 μL sample cell containing BLVRB (0.1 mM). NADP$^+$ mixed BLVRB concentration was calculated at 280 nm wavelength with 14,440+3300 M$^{-1}$ cm$^{-1}$ coefficient using the UV spectrometer.

Data were fitted with a non-linear least-squares routine using a single-site binding model with Origin software (Malvern Instruments), varying the stoichiometry (N), the enthalpy of the reaction (ΔH), the entropy of the reaction (ΔS), the Bibbs free energy of the reaction (ΔG) and the dissociation constant ($K_D$). Data were shown in Table 1 below.

TABLE 1

Representative ITC data for the binding of each compound to BLVRB

| Compounds | N | Temp (° C.) | ΔH (kcal/mol) | TΔS (kcal/mol) | ΔG (kcal/mol) | $K_D$ (μM) |
|---|---|---|---|---|---|---|
| Phloxine B | 0.99 | 25 | −3.88 ± 0.06 | 4.12 ± 0.12 | −8.00 ± 0.10 | 1.36 ± 0.22 |
| Erythrosin B | 1.04 | 25 | −6.38 ± 0.06 | 2.91 ± 0.13 | −9.28 ± 0.11 | 0.16 ± 0.03 |
| Compound of formula 3 | 1.07 | 25 | −4.49 ± 0.06 | 3.50 ± 0.10 | −7.99 ± 0.08 | 1.38 ± 0.18 |
| Compound of formula 1 | 0.99 | 25 | −9.43 ± 0.05 | −0.76 ± 0.07 | −8.67 ± 0.05 | 0.44 ± 0.04 |
| Compound of formula 2 | 0.99 | 25 | −9.79 ± 0.09 | 0.01 ± 0.20 | −9.79 ± 0.18 | 0.07 ± 0.02 |
| Compound of formula 5 | 1.01 | 25 | −5.75 ± 0.08 | 2.14 ± 0.11 | −7.90 ± 0.08 | 1.63 ± 0.21 |
| Compound of formula 4 | 1.02 | 25 | −10.96 ± 0.06 | −1.83 ± 0.09 | −9.13 ± 0.07 | 0.20 ± 0.02 |
| Compound of formula 6 | 1.00 | 25 | −7.32 ± 0.10 | 0.55 ± 0.12 | −7.87 ± 0.07 | 1.71 ± 0.21 |
| Compound of formula 7 | 0.99 | 25 | −8.54 ± 0.04 | 0.41 ± 0.07 | −8.95 ± 0.06 | 0.27 ± 0.03 |
| Compound of formula 8 | 1.01 | 25 | −6.76 ± 0.13 | 1.08 ± 0.17 | −7.84 ± 0.10 | 1.80 ± 0.31 |

The dissociation constants ($K_{DS}$) of all the screened compounds as well as the xanthene-based compounds ranged between 0.07 and 1.8 μM, which are well below our activity cut-off (IC$_{50}$<5 μM1). Thus, all compounds are strong and effective binders to BLVRB. Compared to the previously identified xanthene-based inhibitors, erythrosin B and phloxine B, all the compounds screened in this study display similar or tighter binding affinity. Particular, the compound of formula 2 shows the strongest affinity (0.07 μM) to BLVRB among all the compounds. Furthermore, reducing the size of the compound compared to xanthene-based compounds could reduce specific interactions between BLVRB and compounds, which can be monitored through enthalpic contribution in the ITC data. Binding of all the compounds is mostly driven by enthalpic changes (specific interactions between BLVRB and compounds) except phloxine B. Two additional compounds, erythrosin B and the compound of formula 3, display significant contribution from entropy (31% and 44% of the total binding energy, respectively). These results may imply that bulkiness of xanthene-based drugs (erythrosin B and phloxine B) may energetically support the binding by excluding water molecules from the binding site which is known to increase entropy of water. For the compound of formula 3, the large entropic contribution to ΔG may be explained by the conformational flexibility compared to other compounds. Interestingly, two compounds of formulae 1 and 4 show a decrease of binding entropy. In conclusion, the ITC results support specific interactions between BLVRB and all the screened 8 drug candidates.

While the present invention has been described with reference to the exemplary embodiments thereof, it will be appreciated by those skilled in the corresponding art or those having ordinary knowledge in the corresponding art that the present invention may be modified and altered in various manners without departing from the spirit and technical scope of the present invention that are set forth in the following claims.

Therefore, the technical scope of the present invention should not be limited to the contents described in the detailed description of the specification but should be defined by the claims.

The invention claimed is:

1. Method of increasing platelet counts in a subject, the method comprising administering to the subject a therapeutically effective amount of a compound that inhibits Biliverdin reductase B (BLVRB) activity by blocking a binding site of BLVRB or a pharmaceutically acceptable salt thereof, wherein the compound does not contain xanthene or acridine moiety, wherein the compound is selected from the group consisting of the following formulae 1 to 20:

[Formula 1]
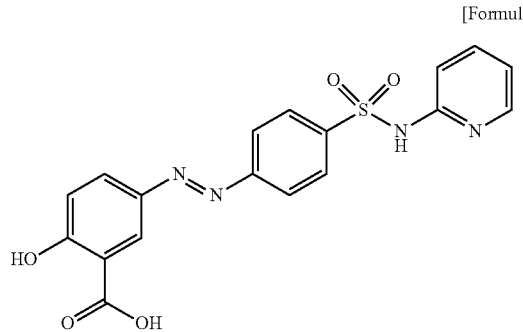
[Formula 5]
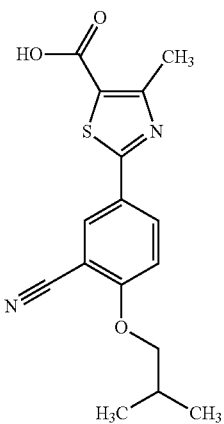
[Formula 2]
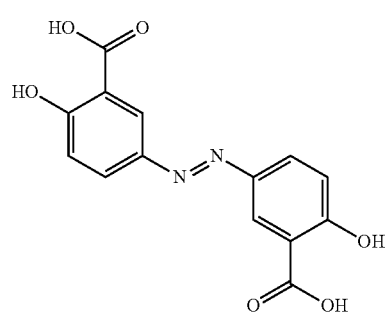
[Formula 6]
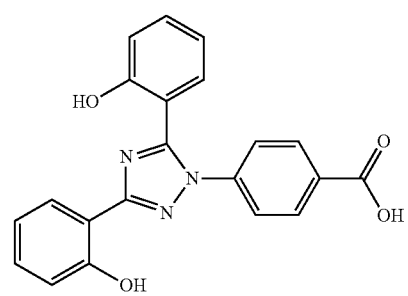
[Formula 3]
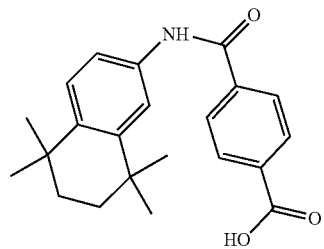
[Formula 7]
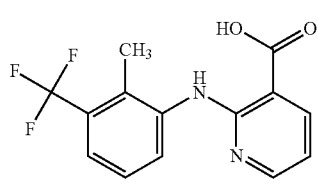
[Formula 4]
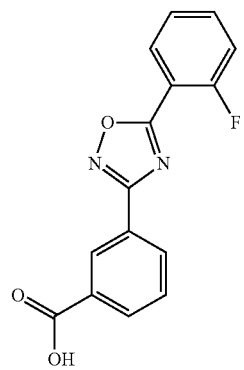
[Formula 8]
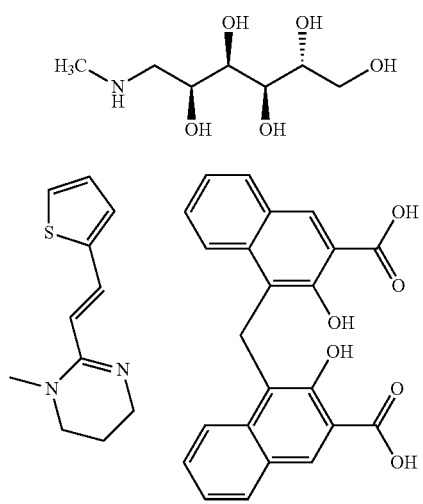

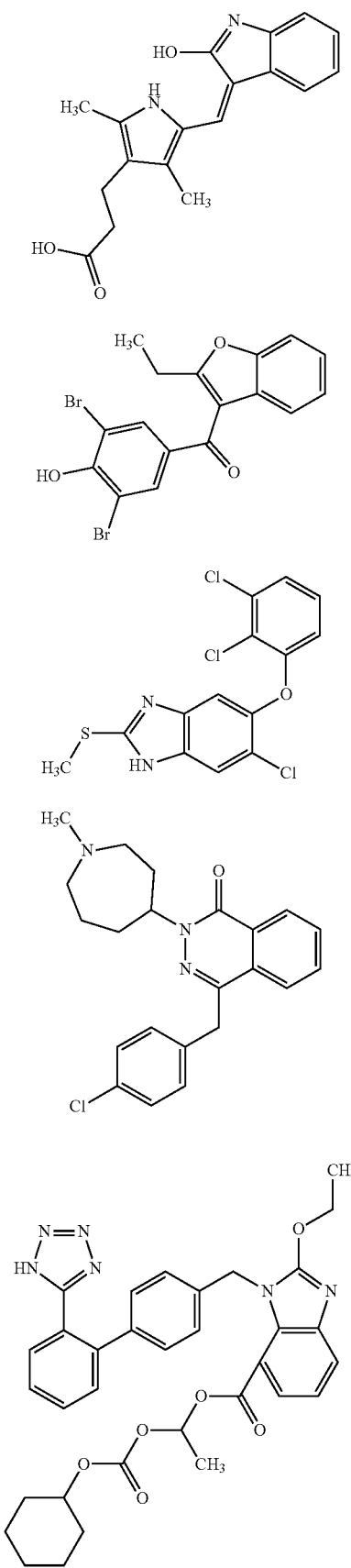
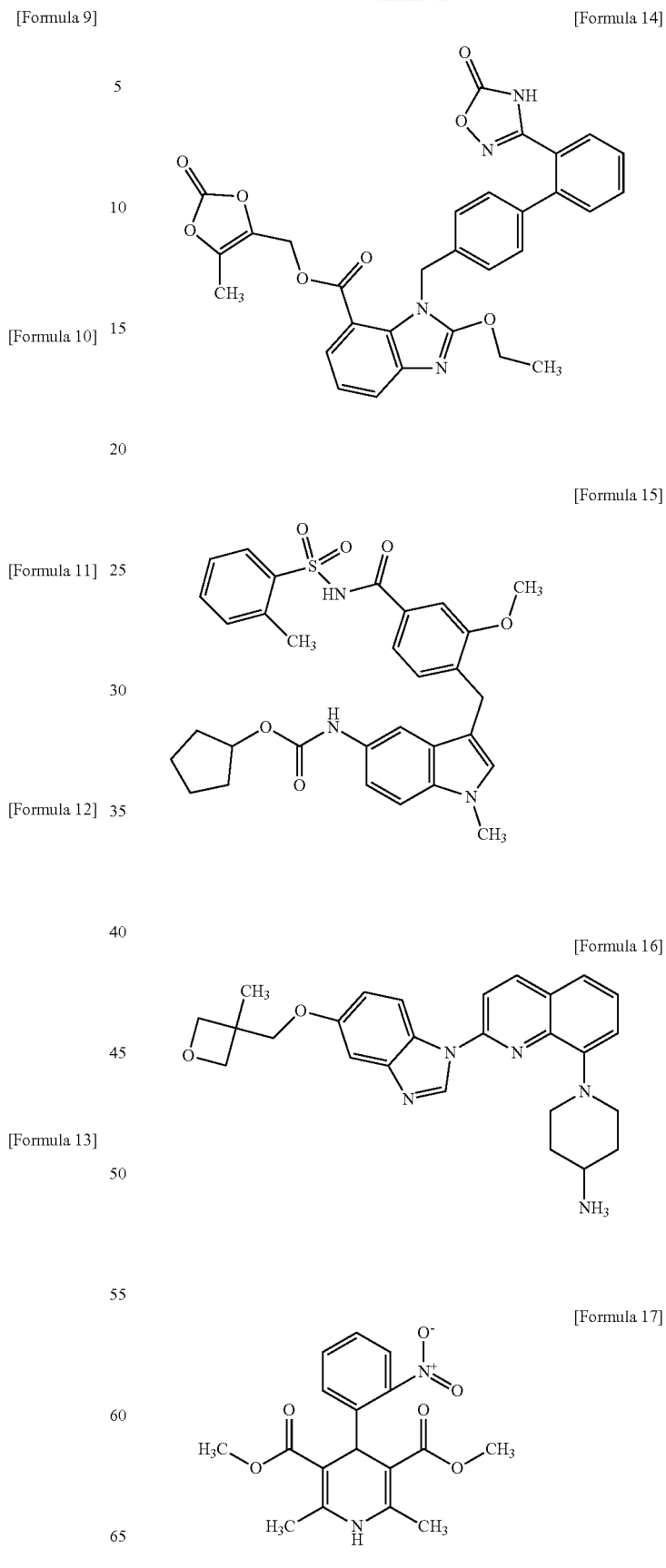
[Formula 9]
[Formula 10]
[Formula 11]
[Formula 12]
[Formula 13]
[Formula 14]
[Formula 15]
[Formula 16]
[Formula 17]

[Formula 18]

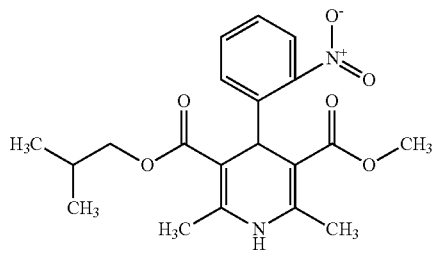

[Formula 19]

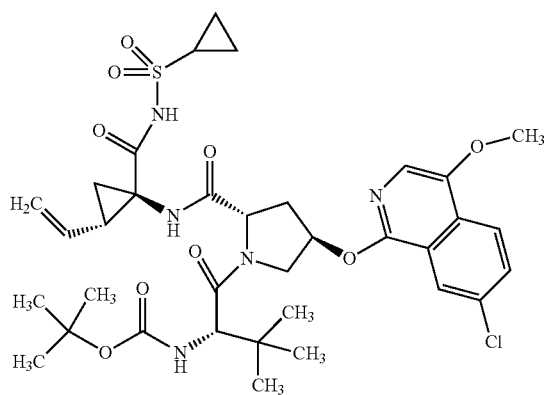

[Formula 20]

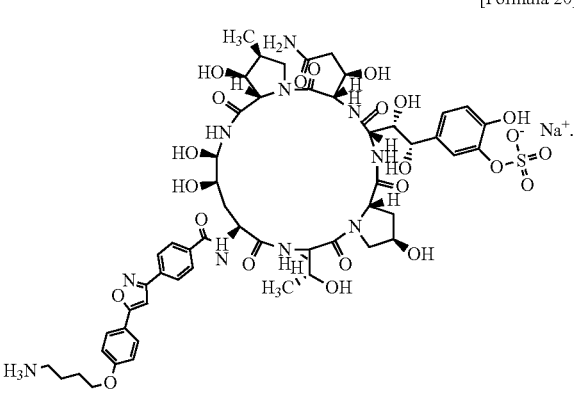

2. The method of claim 1, wherein the compound shows $IC_{50}$ of less than 5 μM.

3. The method of claim 1, wherein the compound is administered in the form of a composition further comprising a pharmaceutically acceptable vehicle.

4. The method of claim 1, wherein the increase of platelet counts treats platelet disorder.

5. The method of claim 4, wherein the platelet disorder is thrombocytopenia.

6. Method of treating platelet disorder, comprising administering to a subject in need a therapeutically effective amount of a compound selected from the group consisting of formulae 1 to 20 above or a pharmaceutically acceptable salt thereof.

* * * * *